(12) United States Patent
Viola

(10) Patent No.: US 9,616,512 B1
(45) Date of Patent: Apr. 11, 2017

(54) INHERENTLY THIN SINGLE WIDTH CHAIN

(71) Applicant: Paul Viola, Bogota, NJ (US)

(72) Inventor: Paul Viola, Bogota, NJ (US)

( * ) Notice: Subject to any disclaimer, the term of this patent is extended or adjusted under 35 U.S.C. 154(b) by 0 days.

(21) Appl. No.: 14/261,532

(22) Filed: Apr. 25, 2014

(51) Int. Cl.
   *B26D 1/46* (2006.01)
   *B23D 61/14* (2006.01)
   *A61B 17/14* (2006.01)

(52) U.S. Cl.
   CPC ............ *B23D 61/14* (2013.01); *A61B 17/141* (2013.01); *A61B 2017/143* (2013.01)

(58) Field of Classification Search
   CPC .. B23D 61/14; A61B 17/141; A61B 2017/141
   USPC ........................ 83/661–845, 698.11; 30/381
   See application file for complete search history.

(56) References Cited

U.S. PATENT DOCUMENTS

| | | | | |
|---|---|---|---|---|
| 1,178,362 A * | 4/1916 | Wall | ................ | B23Q 11/02 83/831 |
| 3,910,147 A * | 10/1975 | Heyerdahl | ................ | 83/830 |
| 4,492,140 A * | 1/1985 | Pano | ................ | 83/839 |
| 4,562,761 A * | 1/1986 | Alexander | ................ | B27B 17/02 83/830 |
| 5,209,216 A * | 5/1993 | Mogi | ................ | 125/21 |
| 5,226,404 A * | 7/1993 | Mogi et al. | ................ | 125/21 |
| 5,725,530 A * | 3/1998 | Popken | ................ | 606/82 |
| 6,178,960 B1 * | 1/2001 | Svensson | ................ | 125/21 |
| 8,398,640 B2 * | 3/2013 | Hawkins et al. | ................ | 606/79 |

* cited by examiner

*Primary Examiner* — Omar Flores Sanchez
(74) *Attorney, Agent, or Firm* — Chan Hubbard PLLC

(57) ABSTRACT

An invention is disclosed comprising a cutting chain of links that pivot without longitudinal disarticulation, yet are connected without reliance on separate connections. Lateral dislocation of the links of the cutting chain is prevented by placement of the cutting chain in a channel, which guides the cutting chain along its operational path and provides resistance against normal load. The channel may be retractable and/or comprised of lubricious, heat absorbing materials. The blade may be flexible in order to cut a variable kerf. The invention further comprises a power train and drive train, designed to optimize the cutting chain for one of many applications.

7 Claims, 5 Drawing Sheets

INHERENTLY THIN SINGLE WIDTH CHAIN

BACKGROUND OF THE INVENTION

1. Field of the Invention

The present invention relates generally to cutting devices using transmission chains, also known as drive chains.

2. Description of the Related Art

A chain saw is a standard example of a cutting device using a transmission chain. Conventional chain saws are comprised of an engine or motor that generates power, a drive mechanism that transmits power from the engine or motor to the chain, a guide bar that guides the chain in an operational path, and a cutting chain that provides a linear cutting surface. In conventional chain saws, such as in FIG. 1, the segments of the cutting chain comprise cutting teeth (links), which are connected by rivets, pins, or any connecting means, including flanking members that are themselves teeth, all of which allow the segments to pivot without disarticulating as the chain is driven forward along the operational path. Drive links of the cutting chain engage with the guide bar, which guides the chain along its operational path and provides resistance against the normal force. The drive links also engage with the drive mechanism, usually comprising one or more sprockets, which power the chain forward as the sprocket turns. Conventional chain saws require the cutting chain to be properly tensioned in order to bear the correct amount of force and to prevent the chain from loosening from the guide bar or sprockets. Tensioning may need adjustment as the chain wears, stretches and/or slackens. In typical power transmission devices, the types and configurations of power trains and drive trains vary according to the device and application. For instance, power sources may be AC, DC, battery, and hydraulic, etc. . . . , and transmissions may include gears of different configurations and sizes.

BRIEF SUMMARY OF THE INVENTION

The present invention comprises a cutting chain of links that pivot without longitudinal disarticulation, yet are connected without reliance on separate connections, such as rivets. Thus it is one object of the invention to reduce the amount of materials needed for manufacture of said cutting chain, reduce the need for lubrication, and allow the cutting chain to be made inherently thin. Lateral dislocation of the links of the cutting chain is prevented by placement of the cutting chain in a channel. The channel also guides the cutting chain along its operational path and provides resistance against normal load. The cutting chain rides in a common plane of operation in the channel, which may be comprised of lubricious or heat absorbing materials. The channel may also be retractable to hide or expose the blade of the chain at selected regions of the path. The blade may also be flexible, bendable, and/or springy in order to cut a variable width kerf. The present invention further comprises a power train and drive train to generate and transmit power to the cutting chain. The power train and drive train system may be designed to optimize the cutting chain for one of many applications. The power train and drive train may be integrated with a motion control system to optimize speed, acceleration, force, torque, power consumption, lubrication, or any other property that is relevant to the cutting operation.

BRIEF DESCRIPTION OF THE DRAWINGS

In the following drawings, like reference numbers have been used wherever possible to indicate like parts in different views.

DETAILED DESCRIPTION OF THE INVENTION

Figure 1:
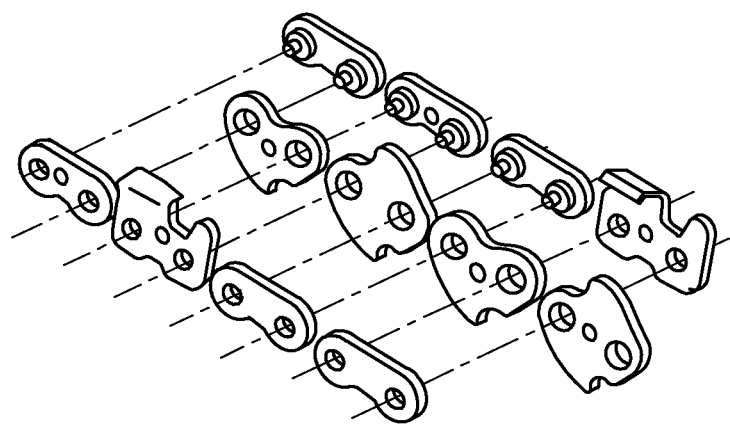
FIG. 1 shows a cutting chain known in the art.
Figure 2:
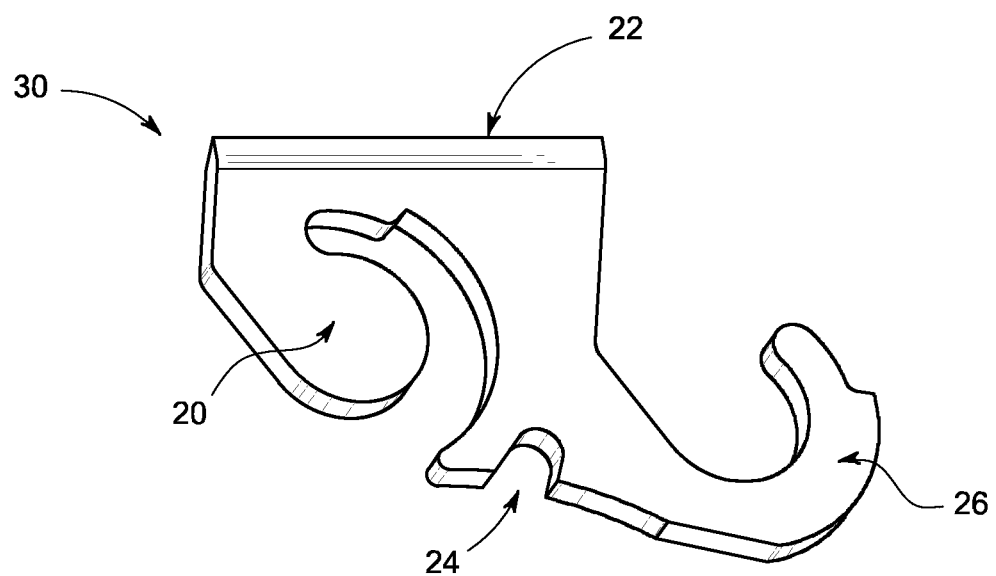
FIG. 2 shows a single cutting chain link.
Figure 3:
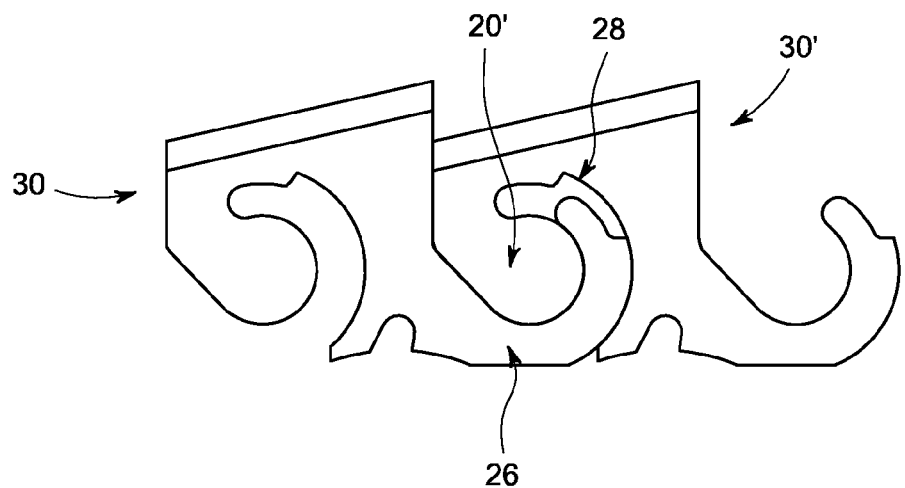
FIG. 3 shows two connected links.

The cutting chain of the present invention comprises a plurality of links that are connected in a common plane of operation and suitable for use in a power transmission device such as a chainsaw. The links are connected by features inherent on the links themselves, which results in an inherently single-width cutting chain. The links are first described with reference to appended drawings FIGS. 2-5. FIG. 2 depicts a single link of the cutting chain in one embodiment of the invention. The link 30 comprises a round feature 20 and a hook feature 26, as well as a cutting edge 22 and a drive cog engagement feature 24. FIG. 3 shows the link 30 connected with a second link 30'. The hook feature 26 of link 30 connects with round feature 20' of link 30', insofar as the hook feature 26 fits into corresponding recess 28. The blade of the link may be any type of blade that is appropriate for the application, including but not limited to standard knife blade or surgical chip tooth blade.

Figure 4:
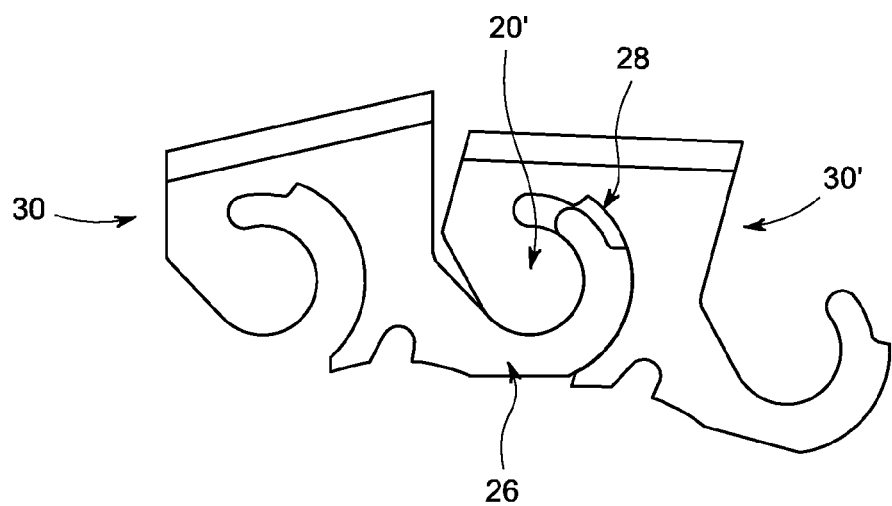
FIG. 4 shows two connected links in a partial rotation position.
Figure 5:
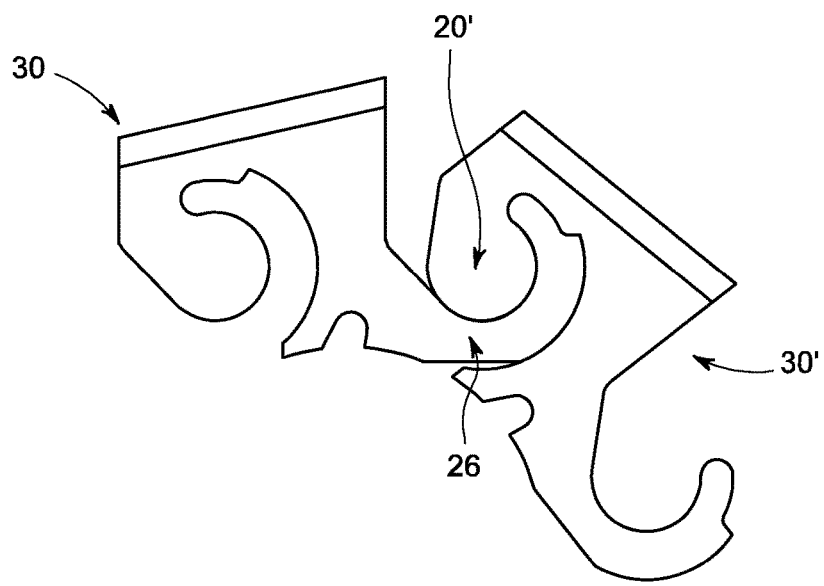
FIG. 5 shows two connected links in a full rotation position.
Figure 6:
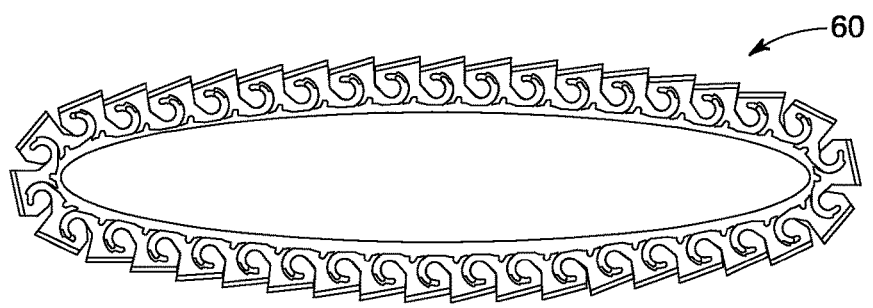
FIG. 6 shows a complete cutting chain of the present invention.

The structure of the hook and round features allows two links to articulate, as illustrated by FIGS. 3-5. Links 30 and 30' may pivot away from each other as far as corresponding recess 28 will allow. FIG. 3 shows the two links 30 and 30' in a non-articulated state, FIG. 4 shows the two links 30 and 30' in a partial pivot away from each other while on a curving operational path, and FIG. 5 shows the two links 30 and 30' in a maximum degree of pivot. Given their structure, as is evident from FIGS. 3-5, the links of the present invention remain connected even as they pivot away from each other along a curving path. The hook and round features of the connected links exert axial distractional force against one another, preventing dislocation of the links by normal force and axial force, no matter the position of the links, i.e. whether the links are articulated or not. Thus, the structure of the hook and round features allow the links to articulate without propensity to disconnect, and without the need for additional mechanical connections such as rivets or pins. A plurality of the described links connect in a common plane of operation to form a chain, which moves along a predetermined path in accordance with the features of the cutting device. Because additional mechanical connections are not needed, the chain is as thin as the material being used to make the links. FIG. 6 depicts an example of an inherently thin chain 60 of links that embodies the current invention.

Figure 7:
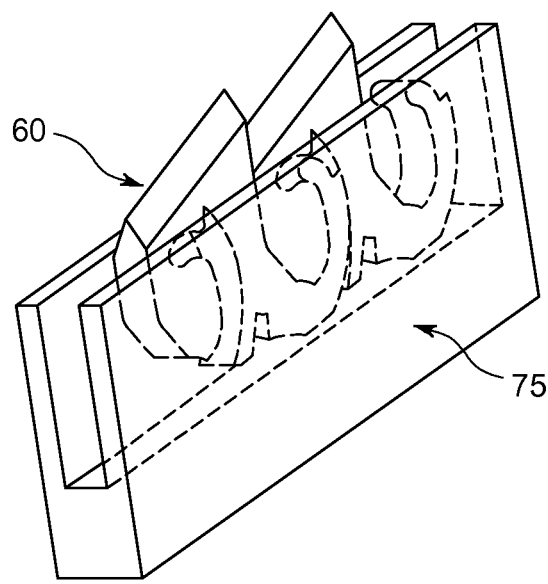
FIG. 7 shows the cutting chain running within a channel.

Lateral dislocation of any two links is prevented by placement of the chain 60 within a channel 75, as depicted in FIG. 7. It will be evident to one of ordinary skill in the art that the channel also functions to guide the chain along the predetermined path and to resist normal forces. The channel may comprise a lubricious material, coatings, and/or surface treatments, which would reduce or eliminate the need for oil and other lubrication during operation. The channel may comprise a heat sink material to draw heat away from the surface of the cutting blade, which would reduce or eliminate the need for lubrication and/or coolant.

Figure 8:
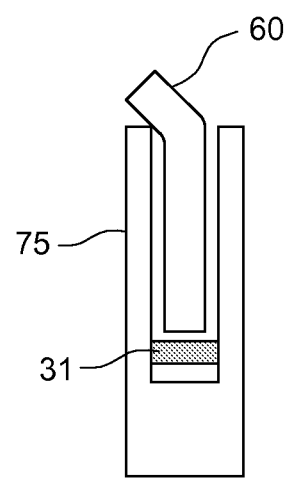
FIG. 8 shows a cross section of the cutting chain running within the channel.

In another embodiment of the invention, the channel may be operable to control the amount or depth of an incision. For instance, using a movable base 31 as depicted in FIG. 8, the channel may cover or expose the cutting blade to a desired depth, or even retract the blade completely when not needed for cutting. One or more links of the cutting blade may furthermore be flexible, bendable, and/or springy, as in FIG. 8, so that when exposed, the blade 60 cuts a kerf that is equal to or wider than the outer thickness of the channel 75. As would be known to one of ordinary skill the art, a flexible link may comprise a material such as spring stainless steel or memory metal. It would also be known to one of ordinary skill that the blade may be of many sizes and structures, including the chip tooth blade depicted in FIG. 8. A chip tooth blade that is retractable and operable to cut an adaptable kerf has many uses in orthoscopic, orthopedic or general surgical instruments.

Figure 9:
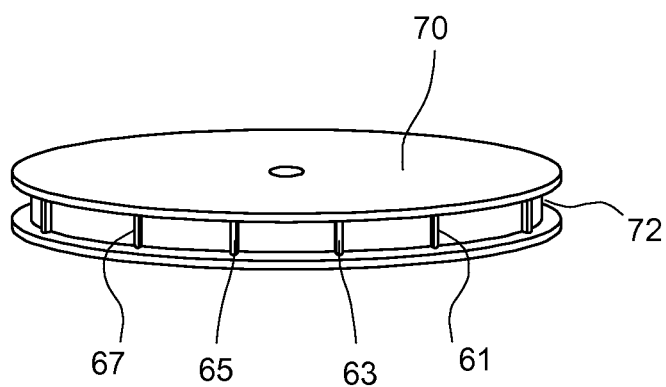
FIG. 9 shows a drive cog.

The cutting device of the present invention is inherently suitable for use in a power transmission device and as such may comprise a transmission apparatus that controllably moves the chain along a predetermined path of operation. For instance, the transmission apparatus may comprise a power train and drive train as is known in the art. One or more gears of the drive train, which may comprise drive gears and idler gears, may further have one or more channels to prevent lateral dislocation of any two links, as described previously. For example, FIG. 9 depicts a drive cog 70 with such a channel 72. The drive cog of FIG. 9 comprises pins 61 through 67 that engage with drive cog engagement features on the links, such as feature 24 on the link 30 in FIG. 2. As will be evident to one of ordinary skill, the drive cog 70 thus drives the chain forward or backwards along the predetermined path of operation.

It will be evident to one of ordinary skill that the gears of the drivetrain of the cutting device of the present invention may be designed in various configurations. For instance, the cutting device may further comprise one or more idler gears, which may have a channel to prevent lateral dislocation. The drivetrain of the present invention may comprise one or more slip clutches allowing torque to be user-controlled. The various gears of the drivetrain of the cutting device may comprise any material or combination of materials, including but not limited to metal, plastic, ceramic, carbon, and carbon fiber. They may also comprise lubricious materials, coatings and/or surface treatments, which would reduce or eliminate the need for oil and other lubrication during operation. In another embodiment of the present invention, the cutting device comprises a lubrication control system, such as a computer controlled system, a timed release system, or lubrication release based on amount of motion or rotation of the chain. The lubricant fluid control system may comprise liquid or gas at ambient, elevated, or cryogenic temperatures. Where the cutting device is used for surgical cutting, for instance, sterile saline may be used as a lubricant, a cooling material, to flush debris, and/or to deliver medication to the subject. The lubricant liquid supplied to the site may also be used as a conduit for electrical and/or sonic energy that may influence the area being cut or enhance a medication to be released at a particular site.

To mount the chain, the links are aligned and linked, then placed within the channel. Mounting may comprise quick release and lock mechanisms as are known in the art.

Tensioning of the chain may be achieved by methods known in the art, such as ratcheting, spring loaded or screw adjusted mechanical means, hydraulic means, or pneumatic systems. Tensioning may be necessary when the chain is first mounted, and adjustments may be further necessary as the chain stretches and/or wears with use.

The appended drawings depict links of identical shape, but it will be evident to one of ordinary skill that links of varying shape may still connect in the manner disclosed in the present invention to form a chain. For instance, a chain may consist of alternating links of two hook features and links of two round features. The chain may consist of links comprising cutting blades of varying shapes, such as bi-directional cutting blades, or no cutting blades. The links may be made of many materials as are known in the art, including but not limited to metal, plastic, ceramic, carbon, and carbon fiber.

Figure 10A:
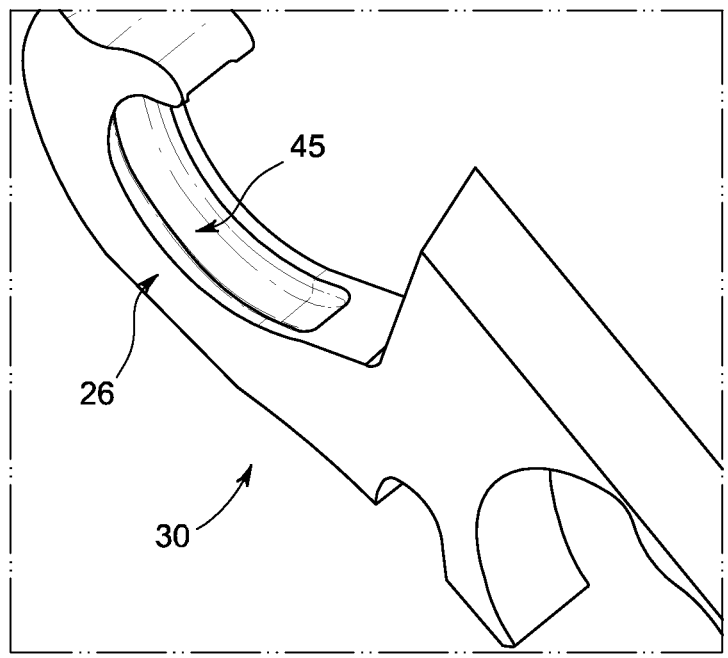
FIGS. 10*a* and 10*b* shows two links having ridge and groove connections.
Figure 10B:
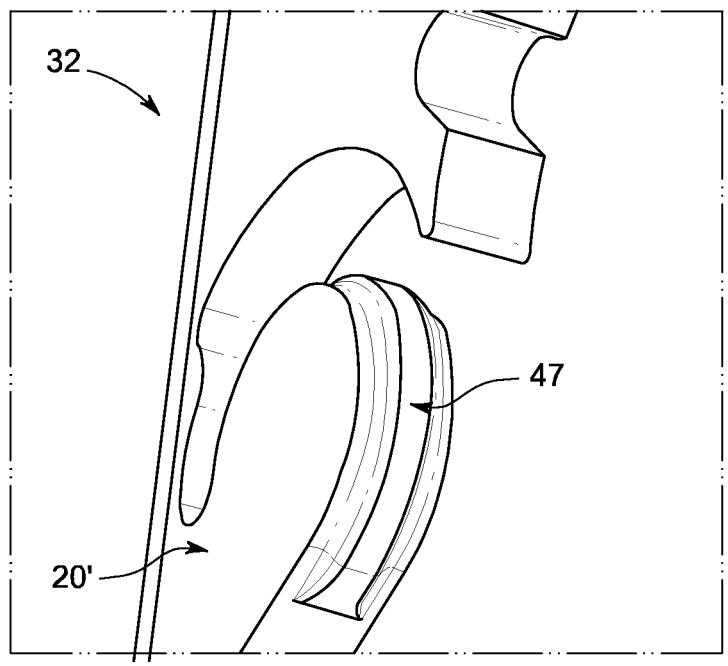

To provide further stability, as may be needed in transit, cleaning, and mounting, for instance, the links may comprise a groove and ridge, as depicted in FIGS. 10a and 10b. In the embodiment depicted in FIGS. 10a and 10b, hook feature 26 of link 30 has a groove 45 and round feature 20' of link 32 has a ridge 47. When links 30 and 32 are connected, the ridge 47 fits into the groove 45 without affecting the full range of rotation of the links. Thus, in an embodiment comprising grooves and ridges, the chain remains naturally in a closed loop even when removed from its mounted position on a device.

The power train may comprise any combination of known and standard power trains, which provide power to the device. Many motors are known in the art and can be used interchangeably in the present invention. For instance, the chain would comprise a rotor and a frame would comprise a stator, in a linear motor system. As would be known to one skilled in the art, the stator is a stationary structure comprising one or more electromagnets, which may be operable in different patterns, intensities and polarities to attract, repel or have no effect on a particular link of the chain. The individual links may be comprised of different materials, so as to be attracted either completely or variably by electromagnetic force. For instance, a link may comprise a permanent magnet of different poles or field orientation, a non-magnetic material, one or more electromagnets, or a material attractive to the magnetic field of a permanent magnet.

The invention may be powered by a conventional rotary fluid or air powered motor using compressed or pressurized fluid such air, nitrogen or water, to produce steady flow, pulsed, metered, or modulated movement. For instance, the chain may be placed in a tunnel with minimal clearance between the chain and the internal walls of the tunnel, wherein the tunnel is pressurized with fluid to move the chain. It will be known to those of skill in the art that compressed and/or pressurized fluid powered motors may be pneumatic, using pressurized gas such as nitrogen or carbon dioxide. Such motors may rely on swappable, built in, rechargeable, or some combination of such pressurized gas cartridges. It is further contemplated that the motor may be coupled to a tank or supply source, such as a water line source, air compressor system, or part of a building.

The invention may be powered by an electrical motor, or any device that can hold, contain or produce electrical current and voltage. For instance, the device may use a DC motor powered by batteries, one or more removable battery packs, rechargeable batteries, or some combination thereof. The device may use an AC motor. It may also be computer controlled, or the motor may be controlled by a Computer Numeric Control (CNC) machine. A pulse or stepper motor may be utilized for complex motion or positioning. Power may also be provided by kinectic or spring mechanisms, or by fuel, steam, or chemical reactions. The device may be powered by hydraulic energy, such as by oil, slurry, water, sterile saline fluid, blood, or other biological fluids.

It will be evident to one skilled in the art that the cutting device may further comprise a system for controlling motion, allowing the chain to be operable and controlled by a user at variable speeds and torque. For instance, torque control may be necessary to prevent stalls, to increase safety, or to reduce the heat associated with the motor, power train, or cutting medium. The motion system may be controlled by trigger, computer, remote control, or voice command. It may be designed to have a zero start speed with an adjustable ramp-up to operating speed. It may control the channel in addition to the blade, for instance to retract, move, or lubricate the channel. It may comprise a temperature feedback system, in which the temperature of a part of the device affects the speed of the cutting chain. Other feedback systems are contemplated, such as systems that adjust for power consumption, temperature, torque, speed, lubrication, force in one or more planes or directions, or acceleration of the tip or edge of the cutting edge.

Power transmission is as known in the art. Gears may be of any design or configuration. Gears may operate to increase or reduce speed and torque, or to reposition the location of the output with or without a reduction or increase in rotational speed. The power transmission system may comprise a fluid pump and motor combination, including by hydraulic or pneumatic systems. Power transmission may be by chain, flexible shaft or speedometer cable, drive shaft, or any combination of mechanical and/or fluid methods for transmitting power. The transmission system may have a slip clutch set at a predetermined torque. It may also comprise a clutch that may be activated to lock or release when actuated by an operator or computer.

As many possible embodiments may be made of the invention without departing from the scope thereof, it is to be understood that all matter herein set forth or shown in the accompanying drawings is to be interpreted as illustrative and not in a limiting sense.

What is claimed is:
1. A chain saw blade link comprising
   (i) a top part having a blade;
   (ii) a bottom part having a drive cog engagement notch;
   (iii) a first side;
   (iv) a second side;
   (v) a round feature extending downward from the top part and inward from the first side towards the center of the link;
   (vi) a hook feature extending upward from the bottom part and outwards from the second side; and
   (vii) a complementary recess shaped to receive an adjacent hook feature, wherein when an adjacent link articulates away from the chain saw blade link on a convex path, the complementary recess receives the adjacent hook feature a complementary recess shaped to receive an adjacent hook feature, wherein when an adjacent link pivots away from the chain saw blade link on a convex path, the complementary recess receives the adjacent hook feature and is completely filled by the adjacent hook feature when the link and the adjacent link are at maximum degree of pivot.
2. The chain saw blade link of claim 1 wherein the hook feature further comprises a groove and the round feature further comprises a ridge.
3. The chain saw blade link of claim 1 comprising a flexible material.
4. A power train blade comprising
   (i) two or more links, wherein each link comprises the chain saw blade link of claim 1; and
   (ii) a channel, wherein the two or more links remain in the channel during operation of the power train blade.
5. The power train blade of claim 4 operable to retract partially or completely into the channel.
6. The power train blade of claim 4 wherein at least one of the two or more links is flexible to cut a variable kerf.
7. The power train blade of claim 4 wherein the channel comprises material, coatings, and/or surface treatments that are lubricious.

* * * * *